US008786825B2

(12) United States Patent
Van De Kerkhof et al.

(10) Patent No.: US 8,786,825 B2
(45) Date of Patent: Jul. 22, 2014

(54) APPARATUS AND METHOD OF MEASURING A PROPERTY OF A SUBSTRATE

(75) Inventors: Marcus Adrianus Van De Kerkhof, Helmond (NL); Maurits Van Der Schaar, Eindhoven (NL); Andreas Fuchs, Meerbusch (DE); Martyn John Coogans, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 491 days.

(21) Appl. No.: 12/936,327

(22) PCT Filed: Apr. 20, 2009

(86) PCT No.: PCT/EP2009/002857
§ 371 (c)(1),
(2), (4) Date: Dec. 22, 2010

(87) PCT Pub. No.: WO2009/129974
PCT Pub. Date: Oct. 29, 2009

(65) Prior Publication Data
US 2011/0102753 A1    May 5, 2011

Related U.S. Application Data

(60) Provisional application No. 61/071,281, filed on Apr. 21, 2008.

(51) Int. Cl.
*G03B 27/54*    (2006.01)
*G03B 27/42*    (2006.01)

(52) U.S. Cl.
USPC ................................. 355/67; 355/53

(58) Field of Classification Search
USPC .................... 355/53, 67; 356/401
See application file for complete search history.

(56) References Cited

U.S. PATENT DOCUMENTS

| 4,200,395 A * | 4/1980 | Smith et al. ............... 356/509 |
| 4,332,473 A * | 6/1982 | Ono .......................... 356/509 |
| 7,791,727 B2 | 9/2010 | Den Boef et al. |
| 2004/0066517 A1 | 4/2004 | Huang et al. |
| 2005/0012915 A1* | 1/2005 | Neijzen et al. ............ 355/53 |
| 2008/0036983 A1 | 2/2008 | De Mast et al. |

FOREIGN PATENT DOCUMENTS

| EP | 1 400 855 A2 | 3/2004 |
| EP | 1 628 164 A2 | 2/2006 |
| WO | WO 2009/078708 A | 6/2009 |

OTHER PUBLICATIONS

International Preliminary Report on Patentability and Written Opinion mailed Nov. 4, 2010 for International Patent Application No. PCT/EP2009/002857, 8 pages.
International Search Report directed to related International Patent Application No. PCT/EP2009/002857, mailed Aug. 4, 2009; 4 pages.

* cited by examiner

*Primary Examiner* — Peter B Kim
(74) *Attorney, Agent, or Firm* — Sterne, Kessler, Goldstein & Fox P.L.L.C.

(57) ABSTRACT

The present invention makes the use of measurement of a diffraction spectrum in or near an image plane in order to determine a property of an exposed substrate. In particular, the positive and negative first diffraction orders are separated or diverged, detected and their intensity measured to determine overlay (or other properties) of exposed layers on the substrate.

25 Claims, 5 Drawing Sheets

APPARATUS AND METHOD OF MEASURING A PROPERTY OF A SUBSTRATE

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

As mentioned above, a pattern is created on the surface of a substrate, this pattern representing the IC, or whatever product is being made on the substrate. The way that the pattern is made is that repeated layers of resist are laid on the substrate, then exposed, then washed or baked or other such post-exposure processes. It is desirable that each of the layers that is to be exposed be aligned with the layer below it such that the pattern builds up as accurately as possible, ensuring effective electrical connections where required and also enabling smaller and smaller products to be created while avoiding cross-talk between neighboring structures. Scatterometers are useful in determining whether or not subsequent layers are aligned as they should be. The alignment of subsequent layers is known as overlay. An error in overlay means that a layer is offset with respect to a layer below (or indeed above) it. If a layer is offset with respect to a layer below it, the quality of electrical contact between structures within these respective layers will be reduced. In extreme cases, complete loss of electrical contact or short-circuiting might occur. The same is true if a product layer is rotated with respect to the product layer below it. These types of overlay error may be measured using scatterometers.

In order to measure and thereby correct for (or, preferably, prevent) overlay errors, test patterns are created on substrates which have known properties and which are tested using a radiation beam and a scatterometer detector, which measures the diffraction spectra of the radiation beam that has reflected from the test pattern. In order to reduce the amount of space taken up by these test patterns, the test patterns are generally created in the scribe lanes between dies and fields on the substrate. It is these scribe lanes that will subsequently be sawn in order to separate the various products, and so are not useful for product. The test patterns are generally known as overlay measurement targets or overlay targets. However, the scribe lanes are small (to leave more room for product) and are also generally packed with a large range of test patterns for various purposes. Because of the relatively large size of the overlay targets, for on-product overlay measurement (i.e. measurement on substrates that also contain product, as opposed to test substrates that may be used purely for testing), in practice, the targets are in the scribe lanes between the dies. However, this means that models are used to predict real product overlay because the real product overlay is not being measured directly.

Models that are used in interpolating scribe lane overlay targets to in-die product are approximations. These approximations may have some errors. The errors may be made worse if fewer targets are available in the scribe lane. It is often the case that fewer than an optimum number of overlay targets are available because the scribe lane "real estate" is valuable to users of lithographic apparatuses (as mentioned above).

To minimize above-mentioned interpolation errors, it is desirable to be able to measure overlay on in-die targets. Because substrate "real estate" is at a premium inside the dies, it is desirable that these overlay targets be as small as possible, and preferably 10 by 10 microns or less. However, with very small targets, there are stringent size requirements which may lead to signal-to-noise ratio problems. Furthermore, signal-to-noise ratios and cross-talk between the overlay target and neighboring product structure may be undesirable. This is because the illuminating beam will be limited to the size that it can be focused down to, which may be larger than the target itself because of the desired extremely small target size.

SUMMARY

It is desirable to provide a technique for measuring overlay that can be carried out on small in-die overlay targets using available alignment radiation beams.

According to an aspect of the invention, there is provided an inspection apparatus, scatterometer, lithographic apparatus or lithographic cell configured to measure a property of a substrate, including: a radiation source configured to output a radiation beam, the radiation beam directed to a surface of the substrate; a collimator configured to collimate and focus the radiation beam once reflected from the surface of the substrate, and to separate diffraction orders of the reflected radiation beam; and a detector configured to detect an angle-resolved spectrum of the reflected radiation beam, wherein the property of the substrate is measured by measuring a property of the reflected spectrum in a plane positioned in a range from where the radiation beam is converging toward an image plane of the collimator to where the radiation beam is diverging from the image plane.

According to another aspect of the present invention, there is provided a method of measuring a property of a substrate, including irradiating a target on a substrate with a radiation beam; reflecting the radiation beam from the target; collimating and focusing the reflected radiation beam using an optical system; diverging first diffraction orders of the reflected radiation beam; detecting the intensity of the first diffraction orders in a plane positioned within a range from where the reflected radiation beam is converging toward an image plane of the optical system to where the reflected radiation beam is diverging from the image plane; and determining, from the intensity of the first diffraction orders, a property of the target of the substrate.

According to yet another aspect of the invention, there is provided a device manufacturing method including using a lithographic apparatus to form a pattern on a substrate; and determining a value related to a parameter of the pattern printed by: irradiating a target on a substrate with a radiation beam; reflecting the radiation beam from the target; collimating and focusing the reflected radiation beam using an optical system; diverging first diffraction orders of the reflected radiation beam; detecting the intensity of the first diffraction orders in a plane positioned within a range from where the reflected radiation beam is converging toward an image plane of the optical system to where the reflected radiation beam is diverging from the image plane; and determining, from the intensity of the first diffraction orders, a property of the target of the substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
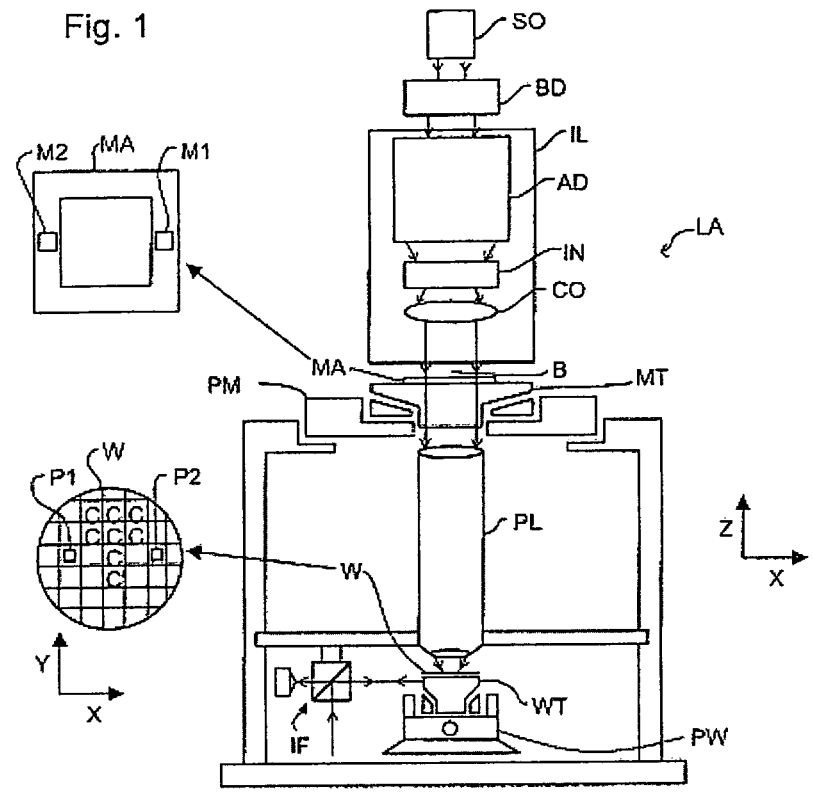
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
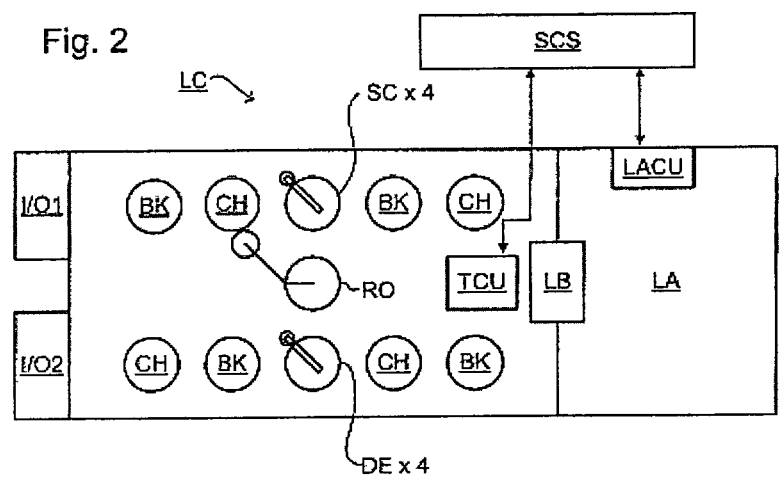
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB), which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
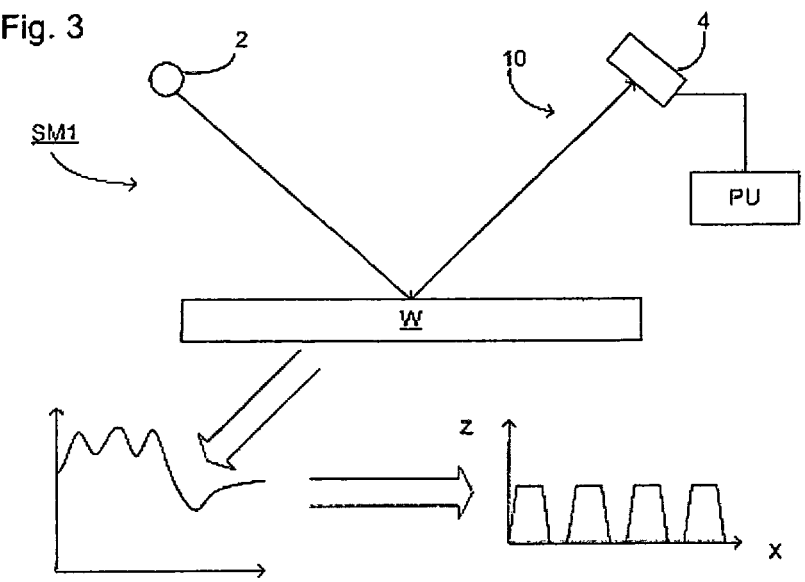
FIG. 3 depicts a scatterometer in accordance with an embodiment of the invention.

FIG. 3 depicts a scatterometer SM1 which may be used in an embodiment of the present invention. It includes a broadband (white light) radiation projector 2 which projects radiation onto a substrate W. The reflected radiation is passed to a spectrometer detector 4, which measures a spectrum 10 (intensity (I) as a function of wavelength ($\lambda$)) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
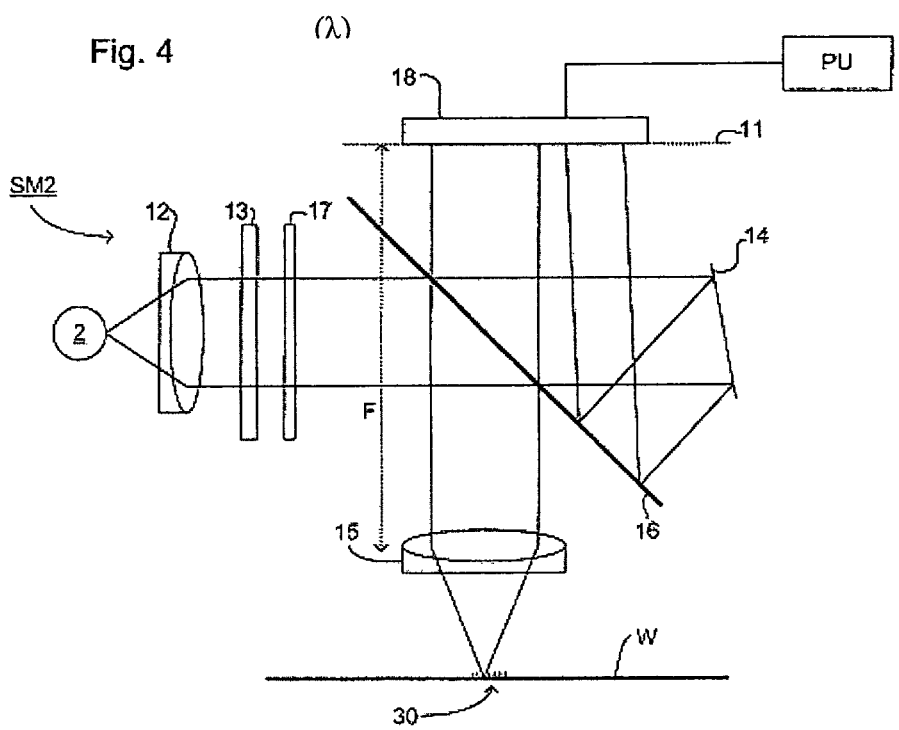
FIG. 4 depicts a scatterometer in accordance with an embodiment of the invention.

Another scatterometer SM2 that may be used with an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation.

The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

Using a broadband radiation or light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

As mentioned above, the scatterometers of FIGS. 3 and 4 may be used to measure the overlay of subsequent exposure layers. The overlay targets that are used for this process are often in the form of periodic gratings. By illuminating this grating first from one direction (at a specific angle of incidence and azimuthal angle) and subsequently from the opposite direction (e.g. same angle of incidence but opposite azimuthal angle), diffraction spectra are created and may be detected, for example in the pupil plane of the objective lens 12.

Illuminating the target first from one direction then from another gives rise to two measurable intensities: one for each radiation beam that has been reflected from each direction. These intensities may then be subtracted from a target image formed by first-order diffracted rays (also produced from the target on the surface of the substrate). The subtraction of the individual intensities from a target image will give rise to an intensity image that shows any asymmetry in the target as a variation in intensity.

However, this method requires two serial exposures with an aperture change in between the exposures. This reduces throughput and may introduce additional error sources (e.g. if the illuminating radiation used in the first direction is not precisely the same as that used in the second direction).

It is therefore proposed here to measure small in-die overlay targets (e.g. 10 by 10 microns) with an image-based technique using a relatively large measurement spot. A measurement spot is the size of the focused illuminating beam. The measurement spot of an embodiment of the present invention may be significantly larger than the overlay target itself. When using an image-based technique, a detector is positioned in the image plane of the optical system that is used to collimate and focus the light reflected from the overlay target. The optical system may be broadly termed hereinafter a collimator. The image plane is a plane in which an image is refocused of an object (i.e. the overlay target in this case) from which radiation has been reflected. If a detector is placed in this image plane, a sharp image of the object will be detected. This is in contrast to other methods, where a detector is placed in a pupil plane of the optical system that is used to collimate and focus radiation reflected from the object to be inspected.

Because of its different position in the collimator, the detector of an embodiment of the present invention may be different from other detectors used in existing scatterometers. Alternatively, existing detectors may be moved, or the optics adjusted so that the image plane of the optical system is positioned at the detector surface.

Figure 5:
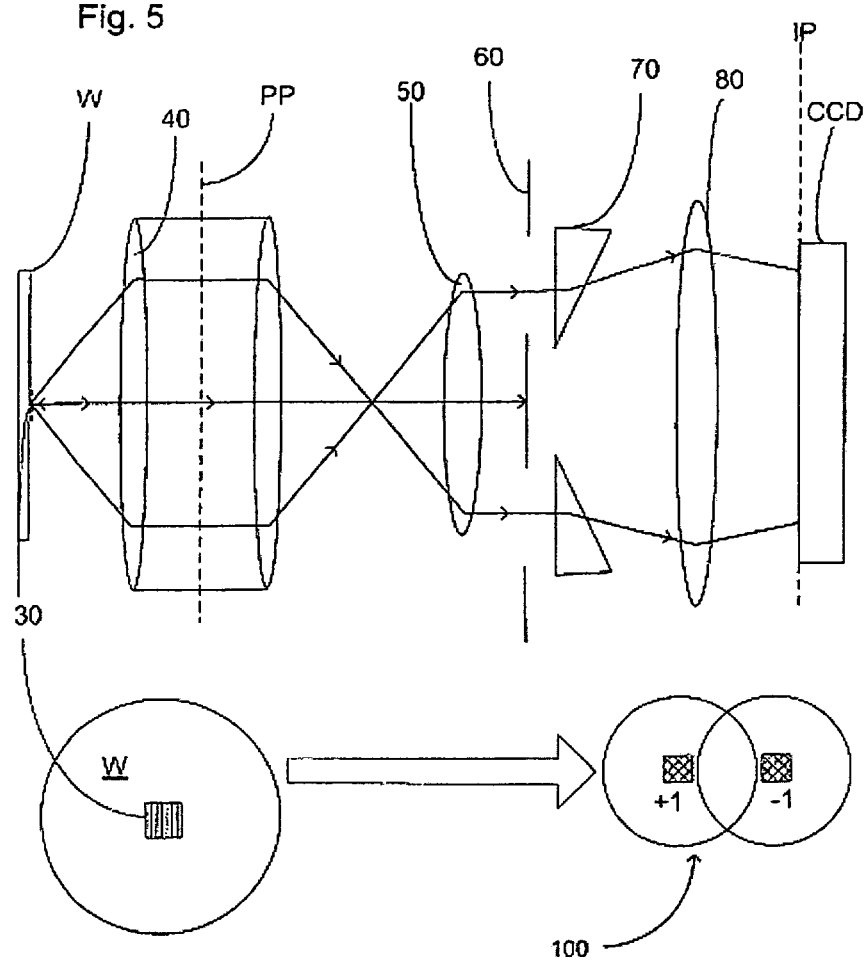
FIG. 5 depicts an illumination set-up according to an embodiment of the invention.

FIG. 5 shows an embodiment of the present invention. A radiation beam is reflected from an overlay target 30 which is positioned on the substrate W. The target may be a grating or other shape that is easily reconstructed or useful for investigating asymmetries in radiation diffracted from it. The overlay target may be in-die; i.e. within the product area rather than in the scribe lanes, thus giving a more accurate indication of the overlay of the product area itself. The target may be very small: smaller than the measurement spot of the radiation beam.

In this embodiment, the optical system or collimator includes a first objective lens 40 that can collimate the diverging beam which has been reflected from the object 30 of the substrate W. A subsequent lens on the other side of a pupil plane PP focuses the reflected radiation beam and causes it to converge to a point in an image plane on the optical axis. The radiation beam, unimpeded, diverges and is again collimated by lens 50.

This reflecting, collimating and focusing of the radiation beam that is carried out by the optical system or collimator gives rise to a diffraction spectrum that is divided into diffraction orders, with the zeroth order in the centre of the radiation beam and progressively higher orders positioned radially outwards. The diffraction spectrum is known as an "angle-resolved" spectrum. As long as the objective lens 40 has a high enough numerical aperture to capture and collimate up to at least the first diffraction orders of the diffracted radiation, the incident radiation may be incident at a large range of angles. The numerical aperture of the objective lens 40 may be increased to over 0.9 and even over 1 with the introduction of a liquid (such as water) between the substrate W and the objective lens 40. This is referred to as "immersion" of the system, as described above.

A spatial filter 60 may be arranged in the second pupil plane of the optical system or collimator. The purpose of the spatial filter 60 is to stop the zeroth diffraction order of the reflected radiation, which is in the center of the diffraction spectrum, from reaching the detector CCD. This creates "darkfield" conditions, thus increasing contrast in the detected image and making asymmetries in the first orders more visible. The spatial filter aids in removing all radiation other than that which has been scattered from an object (i.e. the target 30) which is to be measured. This enables the measurement spot to be larger than the target 30 because non-scattered radiation from an area surrounding the target can be filtered out using the spatial filter 60.

The first diffraction order, which is radially outside of the zeroth order, is allowed to pass through the spatial filter 60. Preferably, only the first diffraction orders are transmitted through the spatial filter 60. Higher diffraction orders should also be also stopped by the spatial filter 60. Each of the positive and negative first diffraction orders that pass through the spatial filter may be subsequently diverged by respective optical wedges 70. This allows the separation of the two first order diffracted beams from each other so that they create a "double vision" effect 100 and are separately detected at the detector CCD. These first order diffracted rays may be subsequently focused by a further lens 80 in order to provide a further image plane IP where the images of the target 30 in the separated first diffraction orders will be focused and sharp. At this image plane IP, the first diffraction orders impinge on the detector CCD.

To prevent these two first diffraction orders from merging into a single image on the camera, an optical wedge 70 may be introduced into the pupil plane (after the spatial filter 60) and into the path of the positive and negative first diffraction orders. Alternatively, wedges with opposite (or at least different) tilts may be applied to both diffraction orders. The optical wedge gives rise to a shift between the two images from the +1 and −1 first diffraction orders such that the two images are separately detected on an image plane IP, but not (necessarily) on the optical axis. This is known as "double-vision" measurement 100.

The double vision effect 100 is caused because the radiation does not converge on the central optical axis of the optical system or collimator to form a single image. Rather, each of the positive and negative first diffraction orders are individually focused using the lens 80 onto separate positions on the detector CCD, thus creating two focused images 100. The two separate images may then be compared.

Both positive and negative first diffraction orders are preferably detected simultaneously, as shown in FIG. 5. In this way, two images are created at the detector of the target 30 from the substrate W. The detected information 100 is shown at the bottom of FIG. 5. On the left is the +1 diffraction order and on the right is the −1 diffraction order. It will be appreciated that, depending on the optical system or collimator, these may be reversed or displayed in a different way.

The intensities of the two images 100 can be compared and the asymmetry in the measured intensities can be linked to the overlay error in the target 30.

Compared to illuminating the overlay target first from one direction and then from another direction, image-based measurement such as that described above has three major benefits. The first is higher throughput. Because different measurements of the same target may be measured simultaneously, measurement of overlay may be carried out more quickly and results fed back to the lithography exposure system, thus increasing the speed at which correctly-exposed substrates may be created. The second benefit is that the system of an embodiment of the present invention is less sensitive to variations between serial exposures. This is because only one exposure of the overlay target 30 is required. A third benefit is that the +1 and −1 diffraction orders are generated by one common incident ray (rather than by two only partly related incident rays). The illuminating radiation is therefore constant, thus giving rise to fewer sources of measurement error.

As a refinement of the method described above, vision analysis can be applied to find accurately the target images in the detector picture. In other words, analysis of the detector signal may be used to determine exactly where on the substrate W the overlay target 30 exists with respect to the optical axis of the sensor optics, and this may be done automatically. This reduces the need for very precise positioning of the detector and the alignment beam with respect to the substrate and its target. Errors of relative positioning may thereby be automatically removed from the overlay calculation. Alternatively, this technique may be used to generate a warning signal to indicate that the positioning of the target with respect to the sensor is not sufficiently good, and that repositioning is needed (including information on direction and magnitude of the repositioning step). This repositioning may also be automated.

Figure 6:
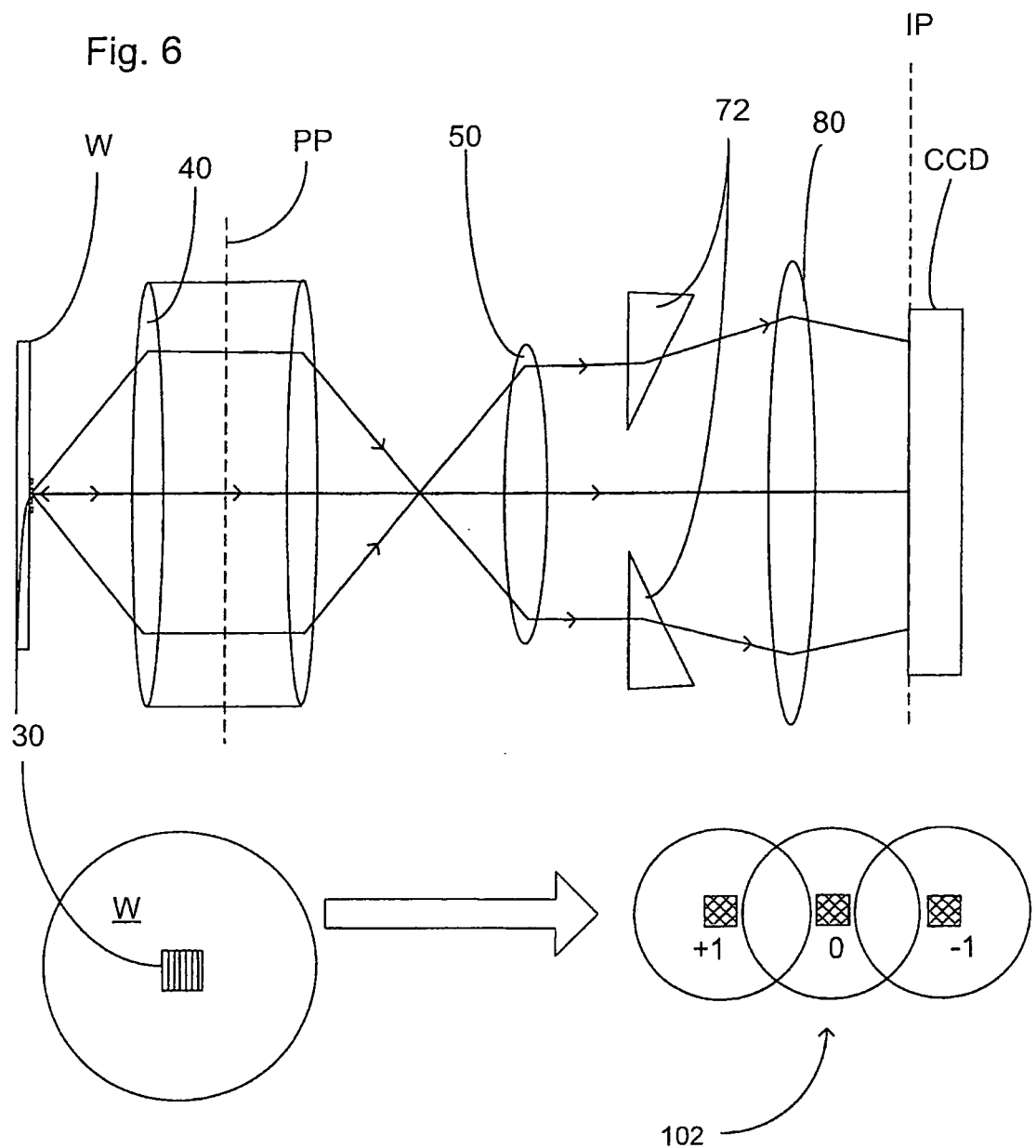
FIG. 6 depicts an illumination set-up according to an embodiment of the invention.

FIG. 6 shows an embodiment of the present invention. The common features are labeled with common reference numerals. The basic set-up is the same, with an objective lens 40 collimating the reflected radiation and the radiation subsequently being focused and re-collimated by lens 50. However, there is no spatial filter (60) in this embodiment for blocking the zeroth order radiation. However, a system of optical wedges 72 is included, which allows three separate target images 102 to be formed as shown in the bottom of FIG. 6.

In the specific embodiment shown, the zeroth and first orders are detected by the detector CCD. However, it is within the scope of the invention to detect higher-order diffracted rays as well. The optical wedges 72 serve to separate out the zeroth diffraction order, which can then be removed from calculations of overlay. The overlay can be calculated again from the two target images from the respective +1 and −1 first-order (and/or higher-order) diffracted rays in the same way as in the first embodiment.

Figure 7:
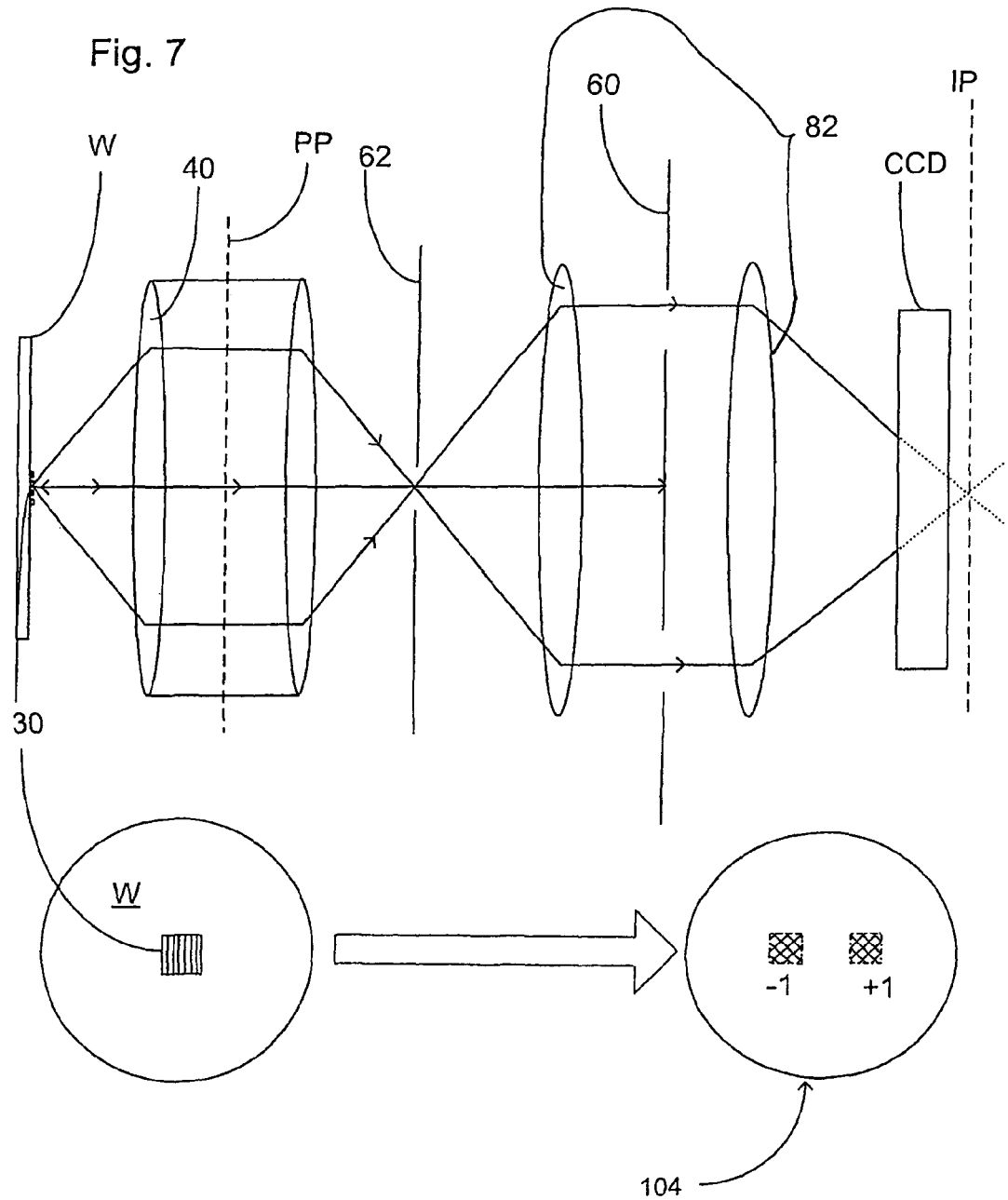
FIG. 7 depicts an illumination set-up according to an embodiment of the invention.

An embodiment of the present invention is shown in FIG. 7. As was the case for the embodiment of FIG. 6, common features with the first embodiment are depicted with common reference numerals. In the embodiment of FIG. 7, the zeroth order diffracted radiation is again blocked using the spatial filter 60, and collimation and focusing of the reflected radiation is carried out in the same way as in the embodiments of FIGS. 5 and 6. However, no optical wedges (70, 72) are used. Instead, the measuring detector CCD is placed not in an image plane IP, but in an intermediate plane between the pupil plane PP,60 and the image plane IP, wherein the radiation is converging from its parallel beam at the pupil plane to a focused point at the image plane IP. Alternatively, and equally validly, the detector CCD may be placed downstream of the image plane IP, wherein the radiation is diverging again after having focused on the image plane IP. Either method results in two spatially separated, blurred images 104 of the target 30.

The embodiment shown in FIG. 7 does not use optical wedges to create the double vision effect (100, 102), but instead, a second set of lenses 82 is used to focus the first diffraction orders toward an image plane IP that is on the optical axis. The blurred target images are separated by the fact that they have not converged together on the axis yet (or have, but are diverging again), rather than by the inclusion of optical wedges to force a focus on an axis other than the main optical axis of the optical system or collimator. The intensity of the blurred images can be measured even though the images are not in focus. The benefit of this embodiment is therefore that the added hardware of optical wedges is not required, and the optical system or collimator can be simplified and manufactured more cheaply.

However, optical wedges may be used as a variation in this embodiment, and the detector may be placed wherever the separated first orders are measurable, whether they are in focus or not.

Again in the embodiment of FIG. 7 or its variation, overlay is calculated from the difference in average intensity of these blurred targets 104.

As a refinement of the embodiment of FIG. 7, a second spatial filter 62 may be employed in an intermediate image plane (which is conjugate to the object plane; i.e. on the same optical axis as the plane in which the object 30 is situated and therefore producing an image with all diffraction orders, which is a full-data image, of the object 30) to prevent rays originating from outside the actual overlay target to be included in the blurred target image. This helps to prevent noise from affecting the intensity measurement at the detector CCD. Furthermore, this enables the measurement spot to be larger than the target on the substrate, enabling the target to be smaller. The first spatial filter 60 may also contribute to this benefit.

The skilled person will be able to envisage within the scope of the claims other set-ups of the apparatus which will enable a detector, or detector array, to be in or near an image plane and to use first (or higher) diffraction orders that are separated from each other to obtain separate signals or images containing only data from the first (and/or higher) diffraction orders. From a comparison of these separate signals or images, an overlay measurement may be determined.

The skilled person will also appreciate that other properties of the substrate may be measured using the techniques described. For example, measurement parameters of an object on the substrate may be reconstructed, such as critical dimension (CD), object height, sidewall angle of the object with respect to the substrate, etc., or alignment of the substrate with respect to an external constant may be measured.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus configured to determine a property of a substrate, comprising:
   a radiation source configured to output a radiation beam toward an overlay target on a surface of the substrate;
   a collimator configured to collimate and focus the radiation beam once reflected from the overlay target, and to separate diffraction orders of a diffraction spectrum of the reflected radiation beam;
   a detector configured to detect at least a subset of the separated diffraction orders of the reflected radiation beam and to determine first and second properties of respective first and second portions of the subset; and
   a processor configured to:
      determine the property of the substrate by comparing the first and second properties in a plane positioned in a range from where the radiation beam is converging toward an image plane of the collimator to where the radiation beam is diverging from the image plane;
      determine a position of the overlay target with respect to an optical axis of the collimator; and
      remove an error of relative positioning from the determination of the property of the substrate based on the determined position of the overlay target.

2. The inspection apparatus according to claim 1, wherein the plane is positioned between an image plane and a pupil plane of the collimator, where, in use, the reflected radiation beam converges towards the image plane.

3. The inspection apparatus according to claim 1, wherein the plane is positioned downstream of a plane conjugate to the image plane, where, in use, the reflected radiation beam diverges from the image plane.

4. The inspection apparatus according to claim 1, wherein the plane is positioned on an image plane of the collimator.

5. The inspection apparatus according to claim 1, wherein the plane is positioned near an image plane of the collimator.

6. The inspection apparatus according to claim 1, further comprising a spatial filter between the substrate and the detector that is configured to block a zeroth diffraction order of the diffraction spectrum.

7. The inspection apparatus according to claim 1, further comprising an optical device configured to spatially diverge positive and negative first diffraction orders of the diffraction spectrum before the spectrum is detected by the detector.

8. The inspection apparatus according to claim 1, wherein the detector is arranged to detect positive and negative first diffraction orders of the diffraction spectrum substantially simultaneously.

9. The inspection apparatus according to claim 1, wherein the property of the substrate to be measured is the overlay of a first layer with respect to a second layer on the substrate.

10. The inspection apparatus according to claim 9, wherein:
    the first measured property comprises a positive first diffraction order and the second measured property comprises a negative first diffraction order; and
    the overlay is measured by comparing intensities of the positive and negative first diffraction orders.

11. The inspection apparatus according to claim 1, wherein the property of the substrate comprises a measurement parameter of the overlay target.

12. The inspection apparatus according to claim 1, wherein the collimator comprises an optical device configured to separate the diffraction spectrum into two or more sub-beams, at least two of the sub-beams comprising non-zero diffraction orders of the reflected beam.

13. The inspection apparatus according to claim 12, wherein:
    the at least two sub-beams comprise a positive and a negative first diffraction order respectively;
    the subset of the separated diffraction orders detected by the detector comprises the positive and negative first diffraction orders of the at least two sub-beams; and
    the processor is configured to determine, from an intensity of each of the two first diffraction orders detected by the detector, an overlay of a first layer on the substrate with respect to a second layer.

14. The inspection apparatus according to claim 1, further comprising a spatial filter positioned in an intermediate image plane of the collimator, the spatial filter being configured to prevent stray radiation from reaching the detector, the stray radiation originating from outside of a target on the substrate from which the radiation beam is reflected.

15. The inspection apparatus according to claim 1, wherein the collimator includes an area between the substrate and a lens that is filled with a fluid configured to create a higher effective numerical aperture of the lens.

16. The inspection apparatus according to claim 1, wherein the detector is configured to detect the diffracted spectrum for a plurality of wavelengths and a plurality of incident angles of the radiation beam substantially simultaneously.

17. The inspection apparatus according to claim 1, wherein the detector is configured to measure defocused images of the surface of the substrate and the property to be measured is determined by analyzing the defocused images.

18. The inspection apparatus according to claim 1, wherein;
    the detector is further configured to output the detected at least subset of the separated diffraction orders as a detector signal.

19. A scatterometer configured to determine a property of a substrate, comprising:

a radiation source configured to output a radiation beam toward an overlay target on a surface of the substrate;

a collimator configured to collimate and focus the radiation beam once reflected from the overlay target, and to separate diffraction orders of an angle-resolved spectrum of the reflected radiation beam; and a detector configured to detect the angle-resolved spectrum of the reflected radiation beam and to determine first and second properties of the angle-resolved spectrum, the detector being situated in a plane positioned in a range from where the radiation beam is converging toward an image plane of the collimator to where the radiation beam is diverging from the image plane; and a processor configured to:
determine the property of the substrate by comparing the first and second properties of the angle-resolved spectrum;
determine a position of the overlay target with respect to an optical axis of the collimator; and
remove an error of relative positioning from the determination of the property of the substrate based on the determined position of the overlay target.

20. A method of measuring a property of a substrate, comprising:
irradiating a target on a substrate with a radiation beam, the radiation beam being reflected from the target as a reflected radiation beam;
collimating and focusing the reflected radiation beam using a collimator;
diverging first diffraction orders of the reflected radiation beam;
detecting the intensity of the first diffraction orders in a plane positioned within a range from where the reflected radiation beam is converging toward an image plane of the collimator to where the reflected radiation beam is diverging from the image plane;
comparing the intensity of each of the first diffraction orders against the other;
determining, from the comparing of the intensity of the first diffraction orders, a property of the substrate;
determining a position of the target with respect to an optical axis of the collimator; and
removing an error of relative positioning from the determining of the property of the substrate based on the determining of the position of the target.

21. The method according to claim 20, further comprising blocking a zeroth diffraction order from the reflected radiation beam.

22. A lithographic apparatus comprising:
an illumination system arranged to illuminate a pattern;
a projection system arranged to project an image of the pattern onto a substrate; and
an inspection apparatus configured to determine a property of the substrate, the inspection apparatus comprising:
a radiation source configured to output a radiation beam toward an overlay target on a surface of the substrate;
a collimator configured to collimate and focus the radiation beam once reflected from the overlay target, and to separate diffraction orders of a diffraction spectrum of the reflected radiation beam;
a detector configured to detect at least a subset of the separated diffraction orders of the reflected radiation beam and to determine first and second properties of respective first and second portions of the subset; and
a processor configured to:
determine the property of the substrate by comparing the first and second properties in a plane positioned in a range from where the radiation beam is converging toward an image plane of the collimator to where the radiation beam is diverging from the image plane;
determine a position of the overlay target with respect to an optical axis of the collimator; and
remove an error of relative positioning from the determination of the property based on the determined position of the overlay target.

23. A lithographic cell comprising:
a coater arranged to coat a substrate with a radiation sensitive layer;
a lithographic apparatus arranged to expose images onto the radiation sensitive layer of the substrate coated by the coater;
a developer arranged to develop images exposed by the lithographic apparatus; and
an inspection apparatus configured to determine a property of the substrate, the inspection apparatus comprising:
a radiation source configured to output a radiation beam toward an overlay target on a surface of the substrate;
a collimator configured to collimate and focus the radiation beam once reflected from the overlay target, and to separate diffraction orders of a diffraction spectrum of the reflected radiation beam;
a detector configured to detect at least a subset of the separated diffraction orders of the reflected radiation beam in a plane positioned in a range from where the radiation beam is converging toward an image plane of the collimator to where the radiation beam is diverging from the image plane; and
a processor configured to:
determine first and second properties of respective first and second portions of the subset, and the property of the substrate by comparing the first and second properties;
determine a position of the overlay target with respect to an optical axis of the collimator; and
remove an error of relative positioning from the determination of the property of the substrate based on the determined position of the overlay target.

24. A device manufacturing method comprising:
forming a pattern on a substrate using a lithographic apparatus; and
determining a value related to a parameter of the pattern formed by:
irradiating a target on the substrate with a radiation beam, the radiation beam being reflected from the target as a reflected radiation beam;
collimating and focusing the reflected radiation beam using a collimator;
diverging first diffraction orders of the reflected radiation beam;
detecting the intensity of the first diffraction orders in a plane positioned within a range from where the reflected radiation beam is converging toward an image plane of the collimator to where the reflected radiation beam is diverging from the image plane;
comparing the intensity of each of the first diffraction orders against the other;
determining, from the comparing of the intensity of the first diffraction orders, the value related to the parameter of the pattern;
determining a position of the target with respect to an optical axis of the collimator; and
removing an error of relative positioning from the determining of the value based on the determining of the position of the target.

25. The device manufacturing method according to claim 24, further comprising blocking a zeroth diffraction order from the reflected radiation beam.

* * * * *

UNITED STATES PATENT AND TRADEMARK OFFICE
CERTIFICATE OF CORRECTION

PATENT NO. : 8,786,825 B2  
APPLICATION NO. : 12/936327  
DATED : July 22, 2014  
INVENTOR(S) : Van De Kerkhof et al.

Page 1 of 1

It is certified that error appears in the above-identified patent and that said Letters Patent is hereby corrected as shown below:

In the Claims

Col. 14, line 62, claim 18, after "wherein", please delete ";" and insert --:--.

Signed and Sealed this
Twentieth Day of January, 2015

Michelle K. Lee
*Deputy Director of the United States Patent and Trademark Office*